US00PP34664P2

(12) United States Plant Patent
Berry

(10) Patent No.: US PP34,664 P2
(45) Date of Patent: Oct. 18, 2022

(54) ***HIBISCUS* PLANT NAMED 'JBG MH-17'**

(50) Latin Name: *Hibiscus rosa-sinensis*
Varietal Denomination: JBG MH-17

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/576,377

(22) Filed: Jan. 14, 2022

(51) Int. Cl.
*A01H 5/02* (2018.01)
*A01H 6/60* (2018.01)

(52) U.S. Cl.
USPC ..... Plt./257
CPC ..... *A01H 6/608* (2018.05); *A01H 5/02* (2013.01)

(58) Field of Classification Search
USPC ..... Plt./257
CPC ... A01H 5/02; A01H 5/00; A01H 6/60; A01H 6/608
See application file for complete search history.

(56) References Cited

U.S. PATENT DOCUMENTS

PP31,854 P3 * 6/2020 Berry ..... A01H 6/608 Plt./257

OTHER PUBLICATIONS

Cpvo Register version 4.1.79, retrieved on Jun. 23, 2022 at https://online.plantvarieties.eu/publicConsultationDetails?registerId=20220609&denomination=jbg%20mh-17, 3 pp. (Year: 2022).*

* cited by examiner

*Primary Examiner* — June Hwu
(74) *Attorney, Agent, or Firm* — The Webb Law Firm

(57) ABSTRACT

A new and distinct *Hibiscus* plant having large, orange and deep reddish purple colored flowers that last for several days on the plant.

2 Drawing Sheets

Botanical classification: *Hibiscus rosa-sinensis.*
Varietal denomination: 'JBG MH-17'.

BACKGROUND OF THE INVENTION

The present invention comprises a new and distinct *Hibiscus* plant having the varietal name 'JBG MH-17'. The new variety is the result of a planned breeding program with the purposes of developing *Hibiscus rosa-sinensis* plants that exhibit whitefly and leaf spot resistance, propagation and production efficiencies, durable and exotic flowers, and abundant flowering. 'JBG MH-17' is the result of a cross conducted in Grand Saline, Tex. between *Hibiscus rosa-sinensis* varieties 'JBG 15010' (female parent, unpatented) and 'JBG 14023' (male parent, U.S. Plant Pat. No. 31,303). The new variety was selected in February of 2016 in Grand Saline, Tex. and the first asexual reproduction of the new variety was conducted by semi-hardwood cuttings in June of 2016 in Grand Saline, Tex. 'JBG MH-17' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG MH-17' is similar to its female parent in flower size and flower color pattern. 'JBG MH-17' differs from its female parent in that the new variety exhibits more saturated flower colors with a ring around the flower eye, more dense branching, and shorter internodes. 'JBG MH-17' is similar to its male parent in flower size and foliage coloration. 'JBG MH-17' differs from its male parent in flower color (orange and deep reddish purple versus creamy white).

When 'JBG MH-17' is compared to *Hibiscus rosa-sinensis* variety 'JBG 14003' (U.S. Plant Pat. No. 31,854), both varieties have a main flower color of orange with concentric color patterns and an eye present. Further, both varieties exhibit an upright flower presentation. However, 'JBG MH-17' has foliage that is darker green in color than 'JBG 14003'. Further, the resistance to bacterial leaf spot is higher with 'JBG MH-17' than 'JBG 14003'.

The following traits distinguish 'JBG MH-17' as a new and distinct cultivar from other *Hibiscus* varieties known to the breeder:

1. Large flower size;
2. High branching;
3. Globe-shaped finished plants; and
4. Very robust and strong growth.

DESCRIPTION OF THE DRAWINGS

The accompanying photographic images illustrate the new variety at approximately twelve months of age, with the colors being as nearly true as is possible with color illustrations of this type.

DESCRIPTION OF THE PLANT

Figure 1:
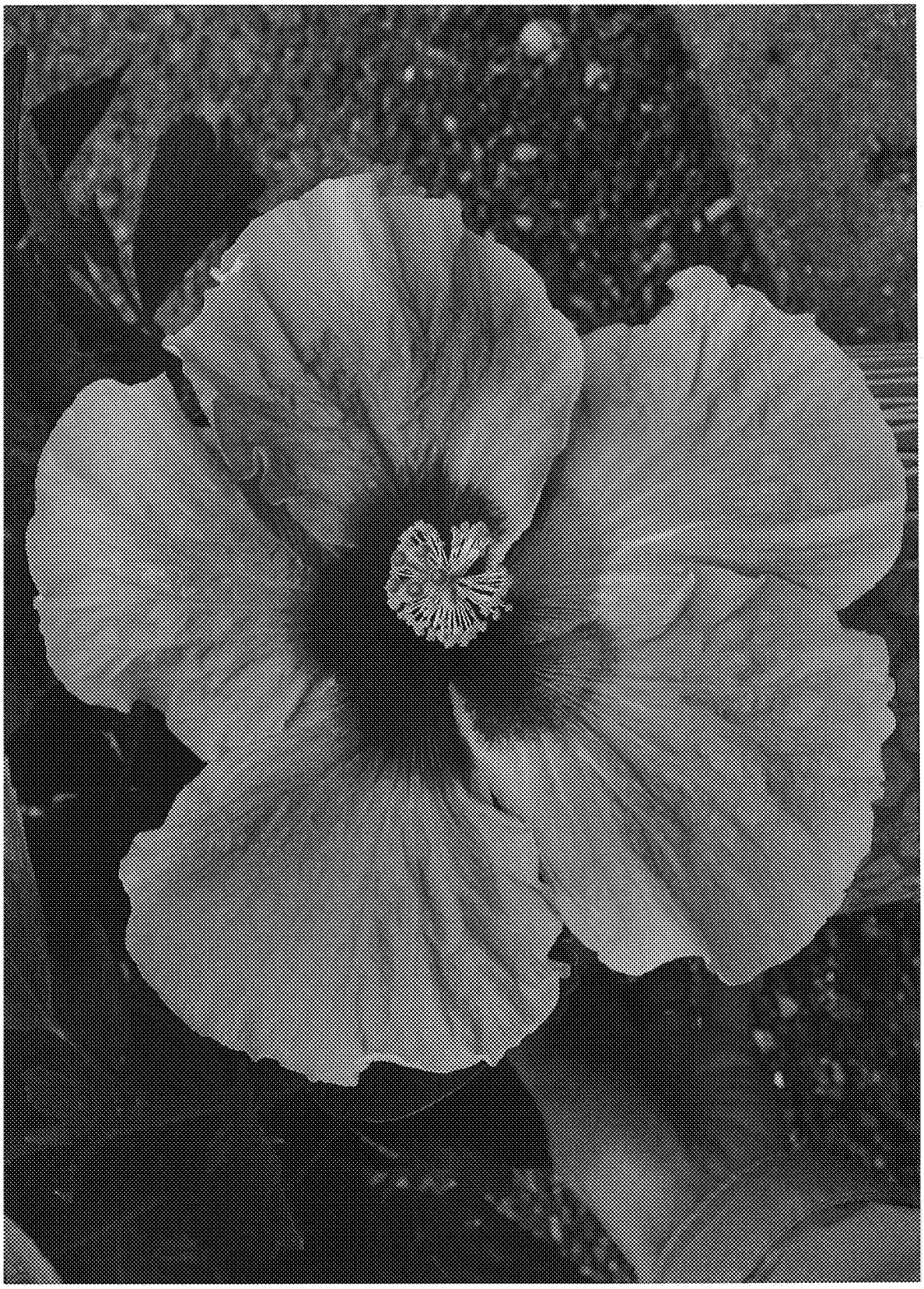
FIG. 1 illustrates a close-up view of a flower of the new variety.
Figure 2:
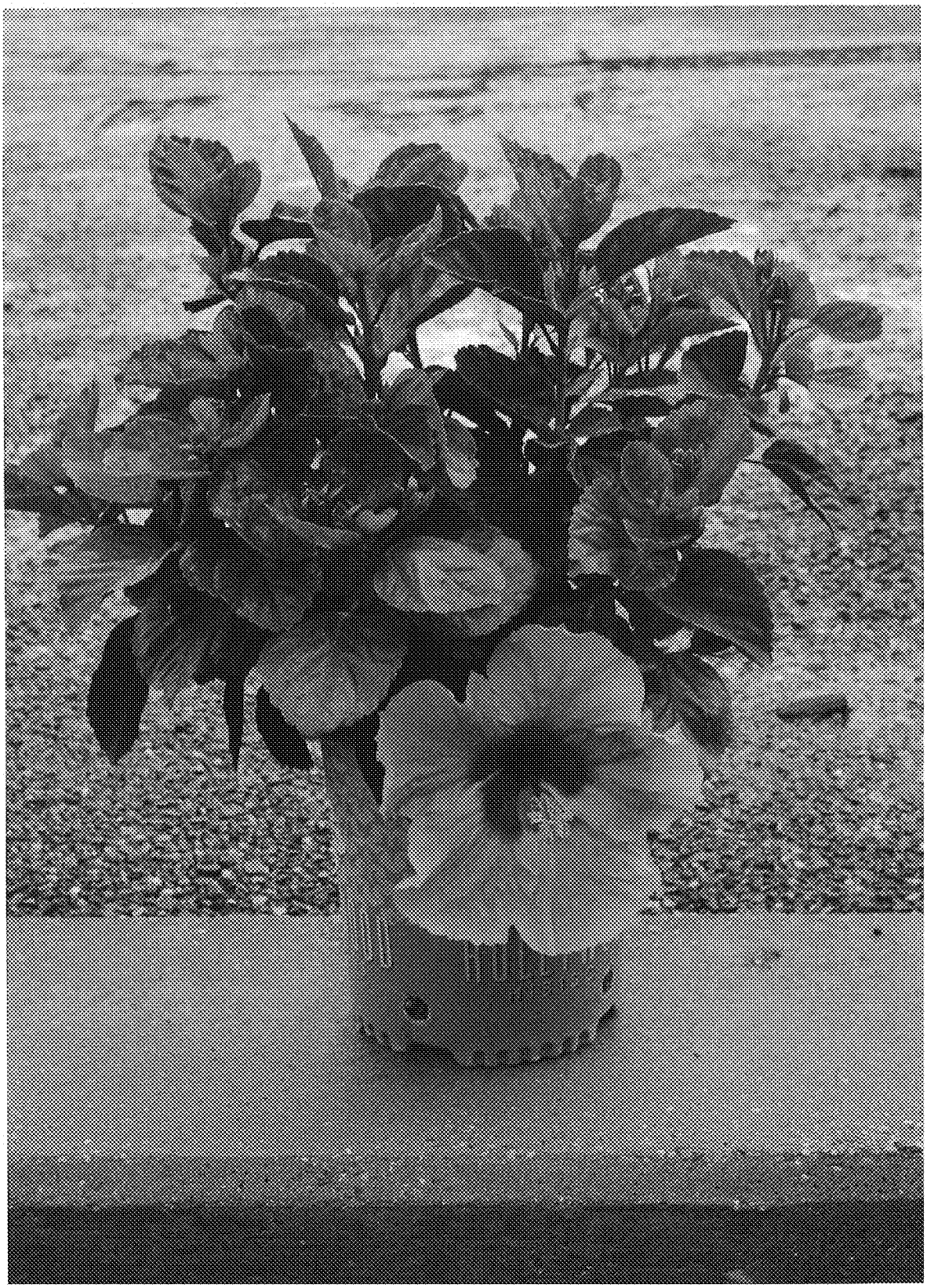
FIG. 2 illustrates a close-up view of an entire plant of the new variety.

The following detailed description sets forth the characteristics of the new variety. The plants were grown in greenhouse heated to a minimum of approximately 13° C. during the cool season, which is otherwise kept at ambient temperatures with a light shade of about 30% in the hot season. The color readings and measurements were taken indoors in Grand Saline, Tex. under fluorescent lighting near natural window light on approximately twelve month old plants that were grown in 2 gallon containers. Color references are primarily to the 1995 R.H.S. Colour Chart of The Royal Horticultural Society of London, 3rd Edition, except where general color terms are used.

PLANT

Time to initiate roots: About 12 days at an average of 24° C.

Time to develop roots: About 50 days at an average of 21-24° C.

Time to produce a finished flowering plant from a rooted cutting: About 12-16 weeks in a 1 gallon/20.0 cm diameter container.

Specific disease/pest resistance: Resistance to whitefly (*Trialeurodes vaporariorum*) and bacterial leaf spot (*Pseudomonas* spp.).

Heat/cold tolerance: Thrives above 24° C., but expires at temperatures of 0° C. and below.

Drought tolerance: Moderate to none.

Plant:

*Type*.—Tropical, ornamental shrub.

*Habit*.—Upright; mounded.

*Height*.—43.2 cm from the top of the pot.

*Spread*.—61.0 cm.

*Vigor*.—Moderate to high.

*Rooting*.—Coarse and well-branched.

Stem:

*Number per plant*.—21.

*Length*.—Ranging from 22.9-35.6 cm.

*Width*.—6.0 mm.

*Texture*.—Immature: Slightly textured. Mature: Coarse, with upright edges.

*Strength*.—Strong.

*Branch number*.—Approximately 18 per stem.

*Internode length*.—3.2-6.4 cm.

*Color*.—Immature: 143A. Mature: 199B.

*Stipules*.—Number per node: 2. Shape: Spinose. Length: 1.0 cm. Width: 1.0 mm. Surface texture: Smooth. Apex: Acute. Base: Linear. Margin: Entire. Color: 143B.

Foliage:

*Arrangement*.—Alternate.

*Size of leaf*.—Length: Approximately 10.0 cm. Width: Approximately 9.5 cm.

*Shape of leaf* (*generally*).—Ovate.

*Shape of apex*.—Acute.

*Shape of base*.—Rounded.

*Texture*.—Upper surface: Smooth and textured from venation. Lower surface: Slightly coarse with texture from venation.

*Margin type*.—Crenate.

*Color*.—Young leaves: Upper surface: 137A. Lower surface: 143A. Mature leaves: Upper surface: 139A. Lower surface: 137A.

*Veins*.—Venation type: Palmate. Color: Upper surface: 139A. Lower surface: 143A.

*Petiole*.—Length: 2.4 cm. Diameter: 3.0 mm. Texture: Mostly smooth. Color: 137A.

FLOWERS

Buds (described in a closed state):

*Shape*.—Acuminate.

*Diameter*.—1.9 cm.

*Length*.—3.8 cm.

*Color*.—137A.

Natural flowering season: Year round in Grand Saline, Tex.

Flower type and habit: Single, with slightly overlapping petals.

Fragrance: None observed.

Flowers:

*Number per stem*.—1.

*Overall depth*.—1.9 cm.

*Overall diameter*.—22.9 cm.

*Shape*.—Rotate.

*Lastingness*.—2-3 days on the plant.

*Petals*.—Number: 5. Arrangement: Simple. Length: 12.7 cm. Width: 11.4 cm. Shape: Ovate. Apex: Obtuse, with incisions absent. Base: Acute. Margin: Entire, with medium undulation intensity. Eye zone size: Medium. Texture/appearance: Upper surface: Smooth. Lower surface: Slightly textured with hair-like extensions. Color: When opening: Upper surface: 32A at end of petal, 54A edging around the eye, and 187B eye color. Lower surface: 33C on left ⅔ of petal and 14B on right ⅓ of petal. Fully opened: Upper surface: 26A at very end of petal that increases in intensity to a central area of 28A, 54A edging around the eye, and 59A eye color. Lower surface: 28C on left ⅔ of petal and 14B on right ⅓ of petal. Venation: 52B.

*Calyx*.—Form: Fused. Overall length: 2.8 cm. Overall diameter: 1.5 cm. Sepals/calyx lobes: Number: 5. Shape: Lanceolate. Apex: Acute. Margin: Entire. Texture: Slightly textured with tiny bumps. Color: Outer surface: 144A. Inner surface: 143C.

*Epicalyx*.—Length: 3.5 cm. Entire width: 1.4 cm. Texture: Inside is smooth and the outside is coarse. Color: 143A.

*Bracts*.—Not present (see epicalyx).

*Peduncle*.—Upper portion length: 1.0 cm that can extend to a total of approximately 7.0 cm. Diameter: 4.0 mm. Strength: Stiff and firm. Angle: Acute. Texture: Slightly textured. Color: 143A.

Reproductive organs:

*Gynoecium*.—Pistils: Number: 1. Length: 9.8 cm. Stigma: Number: 5. Shape: Round. Length: 8.0 mm. Diameter: 1.0 mm. Color: 28A. Style: Length: 8.5 cm. Width: 5.0 mm. Color: 60A. Ovary: Shape: Ovate. Length: 8.0 mm. Width: 5.0 mm. Color: 60A.

*Androecium*.—Stamens: Number: 94. Position: Below the stigma on the style. Anther: Shape: U-shaped. Diameter: 1.0 mm. Color: 23A. Filament: Length: 9.0 mm. Width: 1.0 mm. Color: 69D on the anther end; 61C on the style end. Pollen: Color: 17A. Amount (generally): Moderate.

SEEDS

Seeds:

*Number.*—12.
*Color.*—200A.
*Length.*—5.0 mm.
*Width.*—3.0 mm.

I claim:

1. A new and distinct variety of *Hibiscus* plant named 'JBG MH-17', substantially as illustrated and described herein.

* * * * *